United States Patent [19]

Ochiai et al.

[11] 4,197,298
[45] Apr. 8, 1980

[54] [3-HETEROCYCLIC-7-(2-METHOXYIMINO-2-AMINOTHIAZOLYL) ACETAMIDO]CEPHALOSPORINS

[75] Inventors: Michihiko Ochiai; Akira Morimoto, both of Osaka; Yoshihiro Matsushita, Hyogo, all of Japan

[73] Assignee: Takeda Chemical Industries, Ltd., Osaka, Japan

[21] Appl. No.: 877,761

[22] Filed: Feb. 14, 1978

[30] Foreign Application Priority Data

Feb. 17, 1977 [JP] Japan .................................. 52/16995

[51] Int. Cl.$^2$ .................. A61K 31/545; C07D 501/20
[52] U.S. Cl. ..................................... 424/246; 544/22; 544/27; 544/15
[58] Field of Search ...................... 544/22, 27; 424/246

[56] References Cited

U.S. PATENT DOCUMENTS

| 4,033,950 | 7/1977 | Cook et al. | 544/22 |
| 4,098,888 | 7/1978 | Ochiai et al. | 544/27 |

FOREIGN PATENT DOCUMENTS 852860 9/1977 Belgium .
2556736 6/1976 Fed. Rep. of Germany .

*Primary Examiner*—David E. Wheeler
*Attorney, Agent, or Firm*—Hubbell, Cohen, Stiefel & Gross

[57] ABSTRACT

7-[2-(2-aminothiazol-4-yl)-2-(syn)-methoxyiminoacetamido]cephalosporanic acid derivatives of the formula;

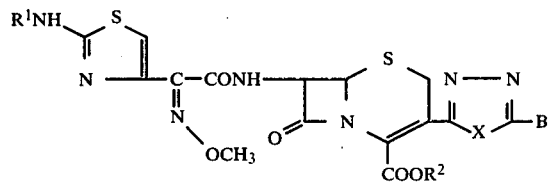

wherein $R^1NH$ is an amino group which may optionally be protected; $COOR^2$ is a carboxyl group which may optionally be esterified; X is oxygen, sulfur or an imino group which may optionally be substituted; B is hydrogen or a hydroxyl, amino, thiol or hydrocarbon group which may optionally be substituted, or a salt thereof, are novel, β-lactamase-resistant and low-toxicity compounds which display excellent activity against a broad spectrum of microorganisms including Gram-negative bacteria such as *Escherichia coli, Serratia marcescens, Proteus rettgeri, Enterobacter cloacae, Citrobacter freundii.* Thus, these compounds can be used for antibacterial agents in therapeutical purpose.

7 Claims, No Drawings

[3-HETEROCYCLIC-7-(2-METHOXYIMINO-2-AMINOTHIAZOLYL) ACETAMIDO]CEPHALOSPORINS

This invention relates to novel 7-[2-(2-aminothiazol-4-yl)-2-(syn)-methoxyiminoacetamido]cephalosporanic acid derivatives of the following formula (hereinafter referred to briefly as "syn"-compounds) and their salts, as well as to processes for the production of said "syn"-compounds and salts.

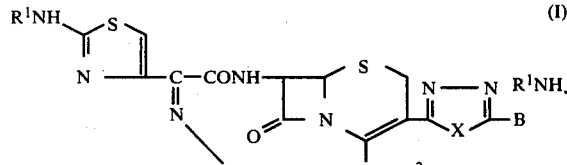

wherein $R^1NH$ is an amino group which may optionally be protected; $COOR^2$ is a carboxyl group which may optionally be esterified; X is oxygen, sulfur or an imino group which may optionally be substituted; and B is hydrogen or a hydroxyl, amino, thiol or hydrocarbon group which may optionally be substituted.

The intensive research undertaken by us led to the finding that, by reacting a compound of the formula:

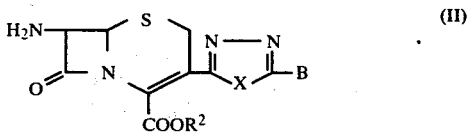

wherein each symbol has the meaning defined hereinbefore, or a salt thereof, with a compound of the formula:

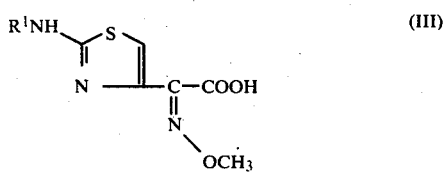

wherein each symbol has the meaning defined hereinbefore, or a reactive derivative thereof or, alternatively, by methylating a compound of the formula:

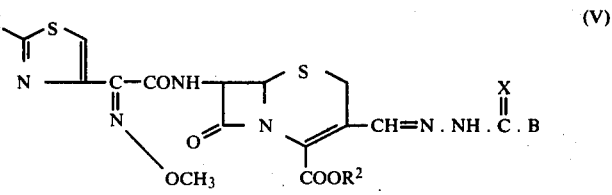

wherein each symbol has the meaning defined hereinbefore, or a salt thereof, and, then, removing the protective group if necessary, or as a further alternative, by subjecting a compound of the formula:

(V)

$$N \overset{R^1NH}{\underset{S}{\diagdown}}\text{...CH}=N.NH.\overset{X}{\underset{\|}{C}}.B$$

wherein each symbol has the meaning defined hereinbefore, or a salt thereof, to oxidative cyclization reaction and, if necessary, removing the protective group, there is obtained the syn-compound (I) or a salt thereof and that said syn-compound (I) and salt thereof have excellent antimicrobial activity. This invention is based on the above finding.

Referring to the above fomulas, $R^1NH$ is an amino group which may optionally be protected. Thus, $R^1$ represents a hydrogen atom or an amino-protecting group. As this amino-protecting group, there may be mentioned any of the per se conventional protective groups commonly employed for the protection of amino groups. Specifically may be mentioned aromatic acyl groups such as phthaloyl, benzoyl, benzoyl group substituted with halogen, nitro or lower alkyls of 1 to 4 carbon atoms (e.g. chlorobenzyl, p-nitrobenzoyl, p-tert-butylbenzoyl, toluoyl, etc.), naphthoyl, phenylacetyl, phenoxyacetyl, benzenesulfonyl and benzenesulfonyl group substituted with lower alkyls of 1 to 4 carbon atoms (e.g. p-tert-butylbenzenesulfonyl, toluenesulfonyl, etc.), camphorsulfonyl, methanesulfonyl, acyl groups derived from aliphatic or halogenated aliphatic carboxylic acids such as acetyl, valeryl, caprylyl, n-decanoyl, acryloyl, pivaloyl, halogenoacetyl(e.g. monochloroacetyl, monobromoacetyl, dichloroacetyl, trichloroacetyl, etc.), and esterified carboxyls such as ethoxycarbonyl, tert-butylxycarbonyl, isobornyloxycarbonyl, phenyloxycarbonyl, trichloroethoxycarbonyl, benzyloxycarbonyl, etc. The formula $COOR^2$ means a carboxyl group which may optionally be esterified. The carboxyl group may be an inorganic or organic salt thereof (e.g. sodium, potassium and other alkali metal or alkaline earth metal salts, trimethylamine salt, etc.). As examples of $R^2$, there may be mentioned lower alkyl (e.g., methyl, ethyl, tert-butyl, tert-amyl, etc.), aralkyl (e.g., benzyl, methoxybenzyl, trityl, benzhydryl, p-nitrobenzyl), etc.), alkanoyloxymethyl (e.g. acetoxymethyl, pivaloyloxymethyl, etc.), di- or tri-alkylsilyl (e.g. trimethylsilyl, etc.), alkoxysilyl, aryl (e.g., 1-indanyl, phthalidyl, 5-indanyl, phenyl, p-nitrophenyl, etc.), alkoxyalkyl (e.g. methoxymethyl, ethoxymethyl, etc.), alkenyl, halogenoalkyl (e.g., trichloroethyl, etc.), alkylsulfonylalkyl (e.g., methylsulfonylethyl, etc.), acylmethyl (e.g., benzoylmethyl, etc.), aralkyloxymethyl (e.g., benzyloxymethyl, etc.), alkylthiomethyl (e.g. methylthiomethyl, etc.), α-acyloxy-α-substituted methyl (e.g. α-acetoxybutyl, α-ethoxycarbonyloxy-α-methylmethyl, etc.) and other ester residues. Such esters are preferably those which can be converted to free carboxyl groups under mild conditions which will not cause a fission of the β-lactam ring. For example, groups such that $R^2$ may be converted to a hydrogen atom under mildly acidic or alkaline conditions, e.g. diphenylmethyl, substituted phenyl, lower alkylsulfonylethyl, pivaloyloxymethyl, etc., and groups such that may be removed by oxidation or reduction, e.g. trichloroethyl, benzyl, etc., may be mentioned. The definition of $-COOR^2$ further includes groups which are ready to be hydrolyzed to $-COOH$, e.g.

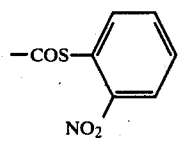

Designated as X is oxygen, sulfur or an imino group which may optionally be substituted. As the substituent on said optionally substituted imino group, there may be mentioned lower alkyl groups (preferably, $C_{1-3}$) such as methyl, ethyl, etc., hydroxyl, mercapto, amino, morpholino, carboxyl, sulfo, carbamoyl, alkoxycarbonyl (preferably, $C_{2-6}$), lower alkylcarbamoyl (preferably, $C_{2-6}$), alkoxyl (preferably, $C_{1-4}$), alkylthio (preferably, $C_{1-4}$), alkylsulfonyl (preferably, $C_{1-4}$), acyloxy (preferably, $C_{2-4}$), morpholinocarbonyl-substituted lower alkyls (preferably, $C_{1-4}$), aryl groups such as phenyl, etc., aralkyl groups such as benzyl, etc., acyl groups (preferably, $C_{1-5}$) such as actyl, propionyl, benzoyl, etc. As substituents on B which may stand for a hydroxyl, amino, thiol, carbamoyl or hydrocarbon group [e.g. alkyls (preferably $C_{1-4}$) such as methyl, ethyl, propyl, isobutyl, tert-butyl, etc.; aralkyl groups such as benzyl, etc., and aryl groups such as phenyl, naphthyl, etc.], there may be employed the above-mentioned and other lower alkyl, acyl(preferably $C_{2-5}$), aralkyl, aryl and other groups. These substituent groups may be further substituted by carboxyl, sulfo, hydroxyl and other groups. In the case of an amino group, it may form a pyrrolidino, morpholino, thiomorpholino or other group as taken together with the N-atom. Thus, as examples of

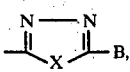

there may be mentioned 5-acetamido-1,3,4-thiadiazol-2-yl, 5-amino-1,3,4-thiadiazol-2-yl, 5-methyl-1,3,4-thiadiazol-2-yl, 1,3,4-thiadiazol-2-yl, 5-acetamido-1,3,4-triazol-2-yl, 5-acetamido-1,3,4-oxadiazol-2-yl, etc.

The syn-compound (I) of this invention is produced by reacting compound (II) or a salt thereof with compound (III) or a reactive derivative of (III), if necessary followed by removal of the protective group or groups. In this method, there are cases in which more satisfactory results are obtained when the reaction of compound (II) or a salt thereof with compound (III) is preceded by the protection of the hydroxyl, amino, thiol, imino, carboxyl or other group in the 3-substituent of compound (II) by a suitable known procedure, although the protective group should then be removed in the known manner after the reaction. As protective groups for this purpose, the protective groups mentioned as to $R^1NH$ as well as the groups commonly employed for the protection of hydroxyl, thiol or carboxyl (such as benzyl, benzhydryl, etc.) may be employed. The compound (III), either in its free form or as a reactive derivative, is used as the acylating agent for acylating the 7-amino group of compound (II). Thus, compound (III) is subjected to the reaction as the free acid (III), a salt of (III) with an alkali metal or alkaline earth metal (e.g. sodium, potassium, etc.) or an organic amine (e.g. trimethylamine, pyridine, etc.), or a reactive derivatives thereof such as an acid halide (e.g. acid chloride, acid bromide, etc.), acid anhydride, mixed acid anhydride, active amide, activated ester and so forth. The active ester thus employed may for example be the p-nitrophenyl ester, 2,4-dinitrophenyl ester, pentachlorophenyl ester, N-hydroxysuccinimide ester, N-hydroxyphthalimide ester or the like. The mixed acid anhydride is exemplified by the mixed anhydrides with carbonic acid monoesters such as monomethyl carbonate, monoisobutyl carbonate, etc. and the mixed anhydrides with lower alkanoic acids which may optionally be substituted by halogen, such as pivalic acid, trichloroacetic acid, etc. Where carboxylic acid (III) is employed as the free acid or in the form of its salt, it is preferable to employ a suitable condensing agent. The condensing agent just mentioned is exemplified by N,N'-disubstituted carbodiimides such as N,N'-dicyclohexylcarbodiimide; azolides such as N,N'-carbonylimidazole, N,N'-thionyldiimidazole, etc.; dehydrating agents such as N-ethoxycarbonyl-2-ethoxy-1,2-dihydroquinoline, phosphorus oxychloride, alkoxyacetylene, etc.; and 2-halogenopyridinium salts (such as 2-chloropyridinium methyl iodide, 2-fluoropyridinium methyl iodide, etc.).

It is likely that, in the presence of such condensing agent, the reaction proceeds via a reactive derivative of carboxylic acid (III). Generally the reaction is conducted in a suitable solvent. As the common examples of such solvent, there may be mentioned halogenated hydrocarbons such as chloroform, methylene dichloride, etc.; ethers such as tetrahydrofuran, dioxane, etc.; dimethylformamide; dimethylacetamide; acetone; and water; as well as mixtures of the solvents mentioned. The acylating agent (III) is generally used in a proportion of about 1 to several mol equivalents to compound (II). Generally this reaction is carried out at a temperature from $-50°$ C. to $+40°$ C. After the acylation reaction, removal of the protective group may be carried out if necessary. Removal of amino-protecting groups can generally be accomplished by procedures known per se [e.g. Japanese published unexamined Patent Application No. 52083/1975; Pure and Applied Chemistry 7, 335 (1963)]or by procedures analogous thereto. The syn-compound (I) thus obtained can be isolated and purified by procedures known per se, e.g. column chromatography, extraction, precipitation, recrystallization, etc. If necessary, (I) may be converted to the desired salt, ester or other compound by procedures known per se.

Further, syn-compound (I) can also be produced by methylating the compound (IV) or a salt thereof and, if necessary, removing the protective group. This reaction is generally carried out in a solvent and at a temperature from ice-cooling to near room temperature and, in many instances, goes to completion within a few minutes to several hours. The solvent may be any solvent that does not interfere with the reaction and is, thus, exemplified by ethers such as tetrahydrofuran, dioxane, etc.; alcohols such as methanol, ethanol, etc.; halogenated hydrocarbons such as chloroform, methylene dichloride, etc.; esters such as ethyl acetate, butyl acetate, etc.; amides such as N,N-dimethylformamide, N,N-dimethylacetamide, etc.; water; and mixtures of such solvents. The methylating agent may be a methylating agent generally employed in organic chemistry, such as methyl halides, e.g. methyl iodide, methyl bromide, etc.; dimethyl sulfate; diazomethane; etc.

There are cases in which this reaction proceeds smoothly in the presence of a suitable base. The base is generally an inorganic base such as alkali metal carbonates (e.g. sodium carbonate, potassium carbonate, etc.) and alkali metal hydroxides (e.g. sodium hydroxide, potassium hydroxide, etc.), although sodium carbonate and potassium carbonate are preferred in view of the stability of compound (IV). This reaction may also be conducted in a buffer solution between pH about 7.5 to about 8.5. The methylation may be followed by removal of the protective group in a manner known per se. The resultant syn-compound can be isolated and purified by the conventional procedures mentioned hereinbefore.

The syn-compound (I) can also be produced by subjecting compound (V) or a salt thereof to oxidative cyclization reaction, if necessary followed by removal of the protective group. This reaction is conducted employing an oxidizing agent which is able to exhibit its action under mild conditions, such as dichlorodicyanobenzoquinone, chloranil, manganese dioxide, ferric chloride, N-chloro- or bromosuccinimide, N-chloro- or bromo-sulfonamide compounds, hydrogen peroxide, peracetic acid, lead tetraacetate, etc. The oxidizing agent is preferably an agent which is active under neutral or weakly acidic conditions, and is desirably one which acts essentially by way of dehydrogenation. Generally this reaction proceeds smoothly in a solvent. Suitable examples of the solvent include ethers (e.g. dioxane, diethylether, etc.), dimethylsulfoxide, dimethylformamide, acetonitrile, nitromethane and so forth. The reaction is desirably conducted at a temperature not exceeding 100° C., and generally goes to completion within 5 hours. The oxidizing reaction may also be conducted by the electrolytic oxidation method. While, depending on the type of oxidizing agent, the cyclization reaction is accompanied by the oxidation of the sulfur atom of the cephem ring, the sulfoxide so formed may then be reduced by the known procedure employing a trivalent phosphorus compound (e.g. phosphorus trichloride, phosphorus tribromide, etc.), a divalent tin or iron compound or the like. An improved yield of cyclization may be expected by subjecting (V) to a preliminary treatment, such as conversion of (V) to the trimethylsilyl, dimethylisobutylsilyl, dimethylsilene, dimethoxydimethylsilyl or dibutyltin ester, for the purpose of enhancing the solubility of (V) or promoting the desired cyclization reaction and, then, permiting said oxidizing agent to act upon the ester or other derivative.

By way of illustration, upon such cyclization reaction, the acetyl compund (V') of cephamthiocarbazone[(V):X=S, B=NH₂]:

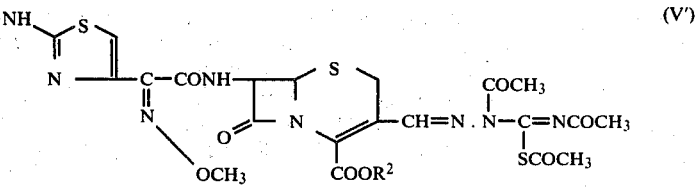

yields the corresponding cephalosporin compound [(I):X=S, B=NHCOCH₃] in quantitative yield. The syn-compound (I) thus produced, after removal of the protective group if necessary, can be isolated and purified by the known procedures such as those mentioned hereinbefore.

The starting compound (II) in this invention can be prepared, for example by the method described in Japanese Published unexamined Patent Application No. 138696/1976 or a modification of the method. The compound (III) can be produced as follows. For example, ① The reaction of a 4-halogeno-3-oxo-2-hydroxyiminobutyric acid derivative of the formula:

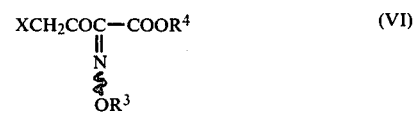

wherein X is halogen, e.g. chlorine or bromine; $R^3$ is hydrogen or methyl; $R^4$ is a lower alkyl of 1 to 3 carbon atoms, e.g. methyl, ethyl or propyl, with thiourea yields a 2-(2-aminothiazol-4-yl)-2-hydroxyiminoacetic acid derivative of the formula:

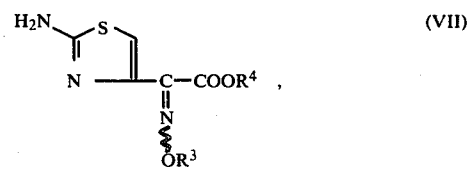

wherein $R^3$ and $R^4$ have the meanings respectively defined above.

Irrespective of $R^3$ being hydrogen or methyl, the resulting compound (VII) generally is a mixture of syn-and anti-isomers. This reaction is generally carried out by reacting compound (VI) with thiourea in an organic solvent such as ethanol, methanol or tetrahydrofuran and at room temperature or elevated temperature.

From the resultant mixture of syn and anti-isomers (VII), the desired syn-isomer can be separated and recovered by a separatory procedure utilizing differences in crystallization behavior or solubility of compound (VII) as it is, or a hydrogen halide salt thereof (HBr, HCl or other salts) or a derivative thereof having a protective group or protective groups as introduced (e.g. monochloroacetyl or dichloroacetyl) into the amino group in 2-position on the thiazole ring; by a chromatographic separation procedure; and by a method of separating the syn-isomer selectively exploiting the difference in the rate of hydrolysis of the syn- and anti-isomers in the hydrolytic coversion, conventional per se, of the ester moiety of compound (VII) or a compound having a protective group as introduced into the 2-amino group of the thiazole ring of (VII) to a carboxylic acid derivative of general formula (III). In the last-mentioned method, the rate of hydrolysis is higher for the anti-isomer than for the syn-isomer, thus permitting a selective hydrolytic removal of the anti-isomer alone. The hydrolysis of the ester moiety of compound (VII) or a derivative thereof having a substituent at the 2-amino group of its thiazole ring is conducted generally in the presence of one to several equivalents of an alkali metal hydroxide such as potassium hydroxide or sodium hydroxide. The reaction proceeds favorably from under ice-cooling to room temperature. This reaction is carried out in a mixture of water and a water-miscible organic solvent such as methanol, ethanol, acetone, tetrahydrofuran, dioxane, N,N-dimethylformamide, N,N-dimethylacetamide or the like. In the case of compound (VII) wherein $R^3$ is hydrogen, the syn-isomer separated may be methylated to the compound in which $R^3$ is methyl. This methylation reaction is conducted generally in a solvent and at a temperature from under ice-cooling to room temperature and, in many cases, goes to completion within a few minutes to several hours. The solvent may be of any type insofar as it does not interfere with the reaction, being exemplified by tetrahydrofuran, dioxane, methanol, ethanol, chloroform, methylene dichloride, ethyl acetate, butyl acetate, N,N-dimethylformamide, N,N-dimethylacetamide, water and mixtures of such solvents. The methylating agent may for example be methyl halide (e.g. methyl iodide, methyl bromide, etc.), dimethyl sulfate or diazomethane. Excepting the case in which diazomethane is employed, the methylation is effected by interacting compound (VII) wherein $R^3$ is hydrogen with said methylating agent in the presence of a base such as an alkali metal carbonate (e.g. sodium carbonate, potassium carbonate, etc.) or an alkali metal hydroxide (e.g. sodium hydroxide, potassium hydroxide, etc.). Some of the physical constants of the resultant syn-isomers of the compound (III) compared with those of the corresponding anti-isomers are shown in the Table 1.

Table 1

| Structure | | NMR spectrum (ppm) | m.p. (°C.) |
|---|---|---|---|
| Syn | $H_2N$—thiazole—C(=N-OH)—COOC$_2$H$_5$ | In δ$_6$-DMSO 6.80s(5-H)11.6s(OH) | 185.5 |
| anti | $H_2N$—thiazole—C(=N-OH)—COOC$_2$H$_5$ | In δ$_6$-DMSO 7.50s(5-H)12.5s(OH) | 145.3 |
| syn | $H_2N$—thiazole—C(=N-OCH$_3$)—COOC$_2$H$_5$ (—COOCH$_3$) | In CDCl$_3$ 6.74s(5-H)4.02s(OCH$_3$) (6.74s) (4.02s) | 163–164 |
| anti | $H_2N$—thiazole—C(=N-OCH$_3$)—COOC$_2$H$_5$ (—COOCH$_3$) | In CDCl$_3$ 7.43s(5-H)4.07s(OCH$_3$) (7.48s) (4.06s) | 114–115 |
| syn | ClCH$_2$CONH—thiazole—C(=N-OCH$_3$)—COOC$_2$H$_5$ (—COOCH$_3$) | In CDCl$_3$ 7.15s(5-H)4.00s(OCH$_3$) (7.24s) (4.02s) | 111–112 |
| anti | ClCH$_2$CONH—thiazole—C(=N-OCH$_3$)—COOC$_2$H$_5$ (—COOCH$_3$) | In CDCl$_3$ 7.94s(5-H)4.10s(OCH$_3$) (8.02s) (4.12s) | 81–82 |
| syn | ClCH$_2$CONH—thiazole—C(=N-OCH$_3$)—COOH | In δ$_6$-DMSO 7.57s(5-H)3.95s(OCH$_3$) | 170–171 |

Table 1-continued

| Structure | NMR spectrum (ppm) | m.p. (°C.) |
|---|---|---|
| anti 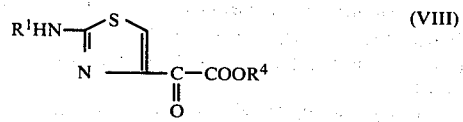 | In $\delta_6$-DMSO 8.00s(5-H)4.00s($OCH_3$) | 182–183 |

Note.
s: singlet
(—$COOCH_3$): the methyl ester of the corresponding compound
Figures in parentheses in the NMR Spectrum column represent the physical constants of methyl esters.

② The following is a description of the process for selective production of compound (III) (syn-isomer). The above reaction of compound (VI) with thiourea to obtain compound (VII) yields a mixture of syn and anti-isomers of (VII) (and, in many instances, the anti-isomer predominates) but our studies on the conditions of this condensing cyclization reaction led us to the finding of conditions under which the desired syn-isomer could be selectively produced. The reaction of compound (VI) with thiourea to produce compound (VII) under the conditions previously mentioned generally yields the syn and anti-isomers in a ratio of 2:98 to 50:50. However, when this cyclization reaction is conducted in a mixture of water and a water-miscible solvent (such as methanol, ethanol, acetone, tetrahydrofuran, dioxane, N,N-dimethylformamide, N,N-dimethylacetamide, N-methylpiperidone, etc.) and in the presence of a basic agent, the syn-isomer is selectively obtained (generally in a ratio of about 85:15 to 100:0). The basic agent employed for the purposes of this reaction is for example an alkali metal or alkaline earth metal salt of a lower aliphatic carboxylic acid or an inorganic or organic base with a pKa value of not less than 9.5 and preferably between pKa 9.8 to 12.0. As examples of the lower aliphatic carboxylic acid salt, there may be mentioned the salts of lower aliphatic carboxylic acids containing 1 to 6 carbon atoms such as sodium acetate, potassium acetate, calcium acetate, barium acetate, sodium formate, sodium propionate, potassium hexanoate, etc. The inorganic base may for example be an alkali metal salt such as sodium carbonate, potassium carbonate or the like. As said organic base, there may be mentioned amines tri-substituted by lower alkyls of 1 to 4 carbon atoms (e.g. trimethylamine, triethylamine, tributylamine, etc.), 5 to 6-membered cyclic amines N-substituted by lower alkyls of 1 to 2 carbon atoms (e.g. N-methylpyrrolidine, N-ethylpyrrolidine, N-methylpiperazine, N-ethylpiperazine, etc.) and the like. Where said N,N-dimethylformamide, N,N-dimethylacetamide or N-methylpyrrolidone is used as the solvent, the aforementioned addition of a basic agent may not be essential.

③ The compound (VII) (syn-isomer) can also be selectively produced by the following process. Our exploratory studies for a method of selective production of the syn-isomer led to the finding that the reaction of an 2-aminothiazol-4-ylglyoxylic acid derivative of formula (VIII)

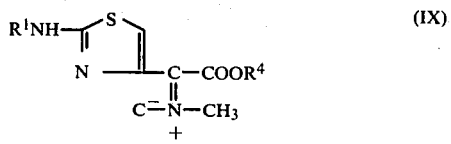

wherein $R^1$ and $R^4$ have the meanings previously defined, with O-methylhydroxylamine selectively yields the syn-isomer with respect to the methoxyimino group. Generally this reaction can be smoothly conducted in a suitable solvent in the pH range of about pH 4.0 to pH 9.0. The solvent may be of any type only if it does not interfere with the reaction. For example, ethers such as ethyl ether, tetrahydrofuran, dioxane, etc.; lower alcohols such as methanol, ethanol, etc.; halogenated hydrocarbons such as chloroform, methylene dichloride, etc.; esters such as ethyl acetate, butyl acetate, etc.; water, and mixtures thereof may be mentioned. While the reaction proceeds in the neighborhood of room temperature, it is accelerated at elevated temperature.

The starting compound (VIII) for this reaction is a novel compound, and can be produced, for example by the following reaction. Thus, hydrolysis of a nitrone compound of the formula:

$$R^1NH-\overset{S}{\underset{N}{\bigsqcup}}-C-COOR^4 \atop C=\overset{|}{N}-CH_3 \atop +$$ (IX)

wherein $R^1$ and $R^4$ have the meanings previously defined, yields compound (VIII). This hydrolysis reaction is caused by a mineral acid, and is generally conducted in a solvent. The mineral acid may for example be hydrochloric acid, sulfuric acid or phosphoric acid. The solvent may be any solvent that will not interfere with the reaction and may for example be an ether (e.g. tetrahydrofuran, dioxane, etc.), an alcohol (e.g. methanol, ethanol, etc.), a ketone (e.g. acetone, methyl ethyl ketone, etc.) or water, or a mixture thereof. This reaction may generally be carried out under ice-cooling to room temperature. The starting compound (IX) is a novel compound which has not been described in the literature, and can be obtained by methylating a compound of general formula (VII) wherein $R^3$ is hydrogen or a compound having a protective group or protective groups as introduced into the 2-amino group of its thiazole ring. The reaction conditions of this methylation are essentially identical with the aforementioned conditions under which the compound (VII) wherein $R^3$ is hydrogen is methylated. Under the described conditions of methylation, methylation of the syn-isomer ($R^3$=H) of compound (VII) does not substantially yield this nitrone compound (IX), while methylation of the anti-isomer ($R^3$=H) of compound (VII) gives the nitrone compound (IX) predominantly. The compound of general formula (VI) may be produced by the methods described in J. Med. Chem. 16, 978(1973), Helv. Chim. Acta. 49, 26(1966), J. Am. Chem. Soc. 60, 1328(1938), German Patent Application DOS No. 2556736, etc. as well as methods analogous thereto.

The reaction of a compound of the following formula (X):

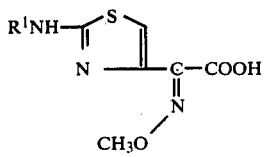

wherein $R^1$ has the meaning previously defined, which is an isomer of compound (III), or a reactive derivative thereof with a compound of formula (II) just as in the case of (III) yields a compound of the formula:

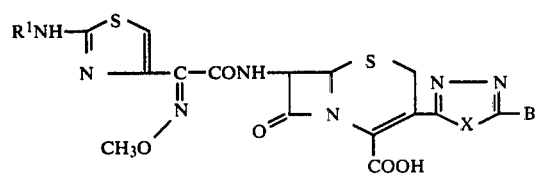

wherein $R^1$, X and B have the same meanings as respectively defined hereinbefore. This compound (XI), too, has excellent antimicrobial activity.

Another starting compound (IV) may be produced, for example by reacting a compound of the formula:

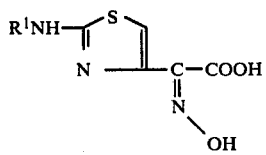

wherein $R^1$ is as previously defined, which can be produced by the above-mentioned process or a reactive derivative thereof with compound (II) or a process analogous to the process described in the specification of DOS No. 2556736. The compound (V) may be produced, for example by the steps of reacting a compound of the formula:

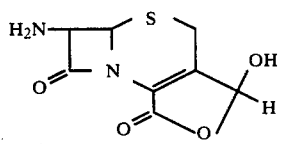

with compound (III) or a reactive derivative thereof to produce a compound of the formula:

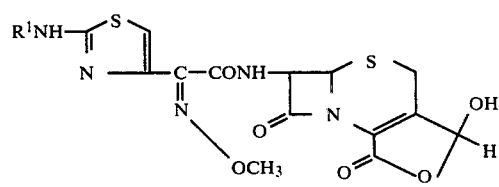

wherein $R^1$ is as previously defined, and, then, reacting (XIV) with a compound of the formula:

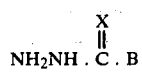

(XV)

wherein X and B are as previously defined or, alternatively, by the method described in Japanese Published unexamined Patent Application No. 138696/1976 or a method analogous thereto.

The syn-compound (I) of this invention, which is obtainable by the above-described method, is considered to have tautomeric structures, i.e. 2-aminothiazole and 2-iminothiazoline, as represented by the following formulas:

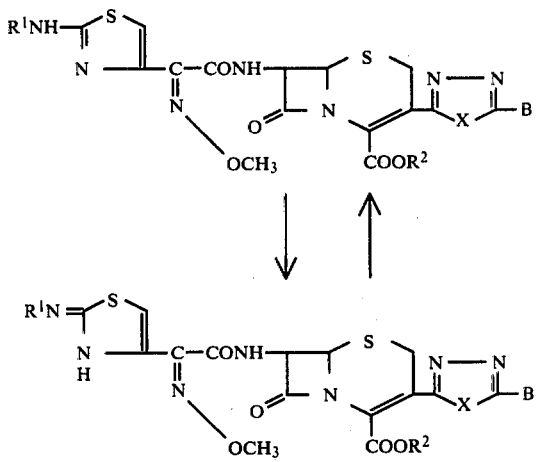

although it is herein designated as the thiazole compound. While the compound of formula (I) may be used as a free compound, it may be used in the form of salts pharmacologically and pharmaceutically acceptable in the general field of cephalosporins or penicillins. For example, the 4-carboxyl group may form a salt with a nontoxic alkali metal cation such as sodium, potassium or the like, a basic amino acid such as arginine, ornithine, lysine, histidine or the like, or a polyhydroxyalkylamine such as N-methylglucamine, diethanolamine, triethanolamine, trishydroxymethylaminomethane or the like; and the amino or imino groups in the 3- and 7-substituents may form salts with inorganic acids such as hydrochloric acid, sulfuric acid, hydrobromic acid, nitric acid, etc. or with organic acids suchas maleic acid, oxalic acid, etc. The compound (I) may also be used in the form of a derivative by converting its 4-carboxyl group to a biologically active ester group conducive to an increased blood concentration or a prolonged efficacy in the body. As the ester residues effective for these purposes, there may be mentioned lower alkoxymethyl groups such as methoxymethyl, ethoxymethyl, isopropoxymethyl, α-methoxyethyl, α-ethoxymethyl, etc.; α-lower alkoxy-α-substituted methyl groups such as α-lower alkoxyethyl, etc.; lower alkyl ($C_{1-3}$) thiomethyl groups such as methylthiomethyl, ethylthiomethyl, isopropylthiomethyl, etc.; acyloxymethyl groups such as pivaloyloxymethyl, α-acetoxybutyl, etc.; ethoxycarbonyloxy-1-methylmethyl or α-acyloxy-α-substituted methyl groups; indan-5-yl; phthalidyl; etc. The compound (I) comprehends those salts and esters of (I).

The compound (I) of this invention can be administered, just as the known cephalosporin and penicillin drugs, either orally or by other routes, in such dosage forms as injections, capsules, powders, granules, tablets and so on which may be prepared in manners known per se. The carrier used in the preparation of such injections may for example be distilled water or physiological saline. To prepare said capsules, powders, granules or tablets, compound (I) is used in admixture with pharmaceutically acceptable excipients known per se (e.g. starch, lactose, sucrose, calcium carbonate, calcium phosphate, etc.), binders (starch, gum Arabic, carboxymethyl-cellulose, hydroxypropyl-cellulose, crystalline cellulose, etc.), lubricants or mold releases (e.g. magnesium stearate, talc, etc.) and disintegrating agents (e.g. carboxymethyl calcium, talc, etc.), for instance.

Thus, the compound (I) is a novel and safe low-toxicity compound which is β-lactamase-resistant, and displays excellent activity against a broad spectrum of microorganisms including Gram-negative bacteria such as *Escherichia coli, Serratia marcescens, Proteus rettgeri, Enterobacter cloacae, Citrobacter freundii*, etc. Therefore, compound (I) can be used as a disinfectant for the removal of said microorganisms, or as a therapeutic agent for the treatment of infectious diseases.

Among various compounds of formula (I), sodium 7-[2-(2-aminothiazol-4-yl)-2-(syn)-methoxyiminoacetamido]-3-(5-acetamido-1,3,4-thiadiazol-2-yl)-3-cephem-4-carboxylate; 7-[2-(2-aminothiazol-4-yl)-2-(syn)-methoxyiminoacetamido]-3-(5-dimethylamino-1,3,4-thiadiazol-2-yl)-3-cephem-4-carboxylic acid or its sodium salt; 7-[2-(2-aminothiazol-4-yl)-2-(syn)-methoxyiminoacetamido]-3-(5-methyl-1,3,4-thiadiazol-2-yl)-3-cephem-4-carboxylic acid or its sodium salt; 7-[2-(2-aminothiazol-4-yl)-2-(syn)-methoxyiminoacetamido]-3-(1,3,4-thiadiazol-2-yl)-3-cephem-4-carboxylic acid; 7-[2-(2-aminothiazol-4-yl)-2-(syn)-methoxyiminoacetamido]-3-(5-acetamido-1,3,4-triazol-2-yl)-3-cephem-4-carboxylic acid or its sodium salt; 7-[2-(2-aminothiazol-4-yl)-2-(syn)-methoxyiminoacetamido]-3-(5-acetamido-1,3,4-oxadiazol-2-yl)-3-cephem-4-carboxylic acid or its salt, for instance, can be safely administered, e.g. for the treatment of infectious diseases such as intraperitoneal infections, respiratory organ infections and urinary tract infections, to mammals including human beings, mice and rats at a daily dose level of 0.5 to 80 mg or, preferably, 1 to 20 mg per kilogram body weight in 3 to 4 divided doses a day.

EXAMPLE 1

In 5 ml of methylene chloride is suspended 133 mg of 2-(2-chloroacetamidothiazol-4-yl)-2-methoxyiminoacetic acid (syn-isomer), followed by addition of 59 mg of triethylamine and, then, 100 mg of phosphorus pentachloride. The reaction is conducted with stirring at room temperature for 20 minutes. To the reaction mixture is added 20 ml of n-hexane and the oily substance obtained by decanting the supernatant is dissolved in 3 ml of methylene chloride. This acid chloride solution is added dropwise to 3 ml of N,N-dimethylacetamide containing 202 mg of diphenylmethyl 7-amino-3-(5-acetamido-1,3,4-thiadiazol-2-yl)-3-cephem-4-carboxylate and the mixture is stirred for 2 hours. Water is added to the reaction mixture which is then extracted with ethyl acetate. The ethyl acetate layer is washed with water, dried and concentrated. By the above procedure is obtained 145 mg of crude diphenylmethyl 7-[2-(2-chloroacetamidothiazol-4-yl)-2-methoxyiminoacetamido]-3-(5-acetamido-1,3,4-thiadiazol-2-yl)-3-cephem-4-carboxylate as powders.

100 mg of the above product is dissolved in 1.5 ml of N,N-dimethylacetamide, followed by addition of 25 mg of thiourea. The mixture is stirred at room temperature for 18 hours. The reaction mixture is added to water and extracted with ethyl acetate. The ethyl acetate layer is washed with water, dried and concentrated. The above procedure yield, diphenylmethyl 7-[2-(2-aminothiazol-4-yl)-2-methoxyiminoacetamido]-3-(5-acetamido-1,3,4-thiadiazol-2-yl)-3-cephem-4-carboxylate. The entire amount of this product is dissolved in 5 ml of trifluoroacetic acid containing 1 ml of anisole and stirred at room temperature for 30 minutes. The reaction mixture is poured into ether and the solid precipitate is collected by filtration. This is dissolved in 0.5 ml of water and the solution is adjusted to pH 7.0 with sodium hydrogen carbonate and purified by passing through a column of Amberlite XAD-2. By the above procedure was obtained 29 mg of sodium 7-[2-(2-aminothiazol-4-yl)-2-methoxyiminoacetamido]-3-(5-acetamido-1,3,4-thiadiazol-2-yl)-3-cephem-4-carboxylate as white powders.

Elemental analysis, for $C_{17}H_{15}N_8O_6S_3Na.4.5\ H_2O$: Calcd. C, 32.53; H, 3.85; N, 17.85: Found C, 32.19; H, 3.29; N, 17.14.

NMR spectrum (60 MHz, in $D_2O$): 2.26 ppm(3H, singlet, $COCH_3$), 4.02 ppm(5H, broad singlet, 2-$CH_2$ & $OCH_3$), 5.37 ppm (1H, doublet, 6-H), 5.92 ppm(1H, doublet, 7-H), 7.01 ppm (1H, singlet, thiazole 5-H).

REFERENCE EXAMPLE 1

To 200 ml of water is added 38 g of sodium nitrite together with 53 g of methyl acetoacetate, followed by dropwise addition of 200 ml of 4 N-sulfuric acid under ice-cooling and stirring over a period of about an hour. During this period, the temperature of the reaction mixture is maintained at 5° to 8° C. The mixture is further stirred within this temperature range for 2.5 hours, at the end of which time it is extracted twice with each 300 ml of ethyl acetate. The extracts are washed twice with a saturated aqueous solution of sodium chloride. Then, a solution of 96.7 g of sodium carbonate in 1 l of water is divided in three parts, which are used to extract methyl 3-oxo-2-hydroxyiminobutyrate from the ethyl acetate layer previously obtained as above (3 times). To the water layer (1 l) was added 200 ml of methanol and, under ice-cooling and stirring, 150 g of dimethyl sulfate is added dropwise over a period of 10 minutes. After the dropwise addition has been completed, the mixture is stirred at room temperature for 1.5 hours. It is then extracted twice with each 300 ml of ethyl acetate, dried and distilled to remove the ethyl acetate. The residue is cooled with ice, whereupon it solidifies. This solid is collected by filtration and rinsed with a small quantity of water. By the above procedure is obtained 52.3 g of methyl 3-oxo-2-methoxyiminobutyrate as white crystals melting at 64.4° C.

Elemental analysis, for $C_6H_9NO_4$: Calcd. C, 45.28; H, 5.70; N, 8.80: Found C, 44.93; H, 5.61; N, 8.71.

NMR spectrum (60 MHz, in $CDCl_3$): 2.40 ppm

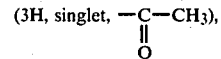

(3H, singlet, $-\underset{\underset{O}{\|}}{C}-CH_3$), 3.86 ppm(3H, singlet, $COOCH_3$), 4.10 ppm(3H, singlet, $=NOCH_3$)

REFERENCE EXAMPLE 2

In 150 ml of chloroform is dissolved 40 g of methyl 3-oxo-2-methoxyiminobutyrate. The solution is warmed to 40° C. and a solution of 40 g of bromine in 50 ml of chloroform is added dropwise over a period of 1 hour. Then, the mixture is further stirred at room temperature for another hour. The reaction mixture is washed with a 5% aqueous solution of sodium hydrogen carbonate and, then, with water. The organic layer is dried and the solvent is distilled off under reduced pressure. By the above procedure is obtained 52.1 g of methyl 4-bromo-3-oxo-2-methoxyiminobutyrate as an oil.

NMR spectrum (60 MHz, in CDCl$_3$): 3.82 ppm(3H, singlet, COOCH$_3$), 4.09 ppm(3H, singlet, =N—OCH$_3$), 4.27 ppm(2H, singlet, BrCH$_2$CO).

In 350 ml of tetrahydrofuran is dissolved 52 g of methyl 4-bromo-3-oxo-2-methoxyiminobutyrate, followed by addition of 250 ml of water. Then, 89.1 g of sodium acetate trihydrate and 33.2 g of thiourea are added and the mixture is reacted with stirring at room temperature for 18 hours. To this reaction mixture is added 200 ml of a 5% aqueous solution of sodium hydrogen carbonate and the mixture is extracted with ethyl acetate. The organic layer is washed with water, dried and distilled under reduced pressure to remove the solvent. To the residue is added 200 ml of ether and the resultant crystals are collected by filtration. By the above procedure is obtained 24.8 g of methyl 2-(2-aminothiazol-4-yl)-2-methoxyiminoacetate (syn-isomer) as crystals melting at 164.9° C.

Elemental analysis, for C$_7$H$_9$N$_3$O$_3$S: Calcd. C, 39.06; H, 4.21; N, 19.52: Found C, 38.78; H, 4.15; N, 19.33.

NMR spectrum (60 MHz, in CDCl$_3$): 3.84 ppm(3H, singlet, COOCH$_3$), 4.02 ppm(3H, singlet, =NOCH$_3$), 5.74 ppm(2H, broad singlet, NH$_2$), 6.74 ppm(1H, singlet, thiazole 5-H)

REFERENCE EXAMPLE 3

In 90 ml of N,N-dimethylacetamide is dissolved 21.5 g of methyl 2-(2-aminothiazol-4-yl)-2-methoxyiminoacetate (syn-isomer) and, under ice-cooling, 13.6 g of chloroacetyl chloride is added dropwise. The mixture is stirred under ice-cooling for 30 minutes and, then, at room temperature for 30 minutes, after which 500 ml of water is added. The mixture is extracted twice with ethyl acetate and the combined extract is washed with a 5% aqueous solution of sodium hydrogen carbonate and water in that order and dried. On removal of the solvent, there is obtained 25 g of methyl 2-(2-chloroacetamidothiazol-4-yl)-2-methoxyiminoacetate(-syn-isomer) as crystals melting at 130.8° C.

Elemental analysis, for C$_9$H$_{11}$N$_3$O$_4$SCl: Calcd. C, 37.05; H, 3.45; N, 14.40: Found C, 37.30; H, 3.40; N, 14.35.

NMR spectrum (60 MHz, in CDCl$_3$): 3.90 ppm(3H, singlet, COOCH$_3$), 4.02 ppm(3H, singlet, =NOCH$_3$), 4.26 ppm(2H, singlet, ClCH$_2$CO), 7.24 ppm(1H, singlet, thiazole 5-H).

REFERENCE EXAMPLE 4

In a mixture of 170 ml water and 900 ml ethanol is dissolved 19.2 g of potassium hydroxide, and 20 g of methyl 2-(2-chloroacetamidothiazol-4-yl)-2-methoxyiminoacetate (syn-isomer) is added. The mixture is stirred at room temperature for 2 hours, after which the ethanol is distilled off under reduced pressure. After the addition of 170 ml of water, the mixture is washed with 200 ml of ethyl acetate. The water layer is adjusted to pH 2 with 10% hydrochloric acid and extracted twice with each 300 ml of ethyl acetate. The extracts are combined, washed with a saturated aqueous solution of sodium chloride and dried. The solvent is distilled off, whereby 16.8 g of 2-(2-chloroacetamidothiazol-4-yl)-2-methoxyiminoacetate (syn-isomer) is obtained as crystals melting at 170°–171° C.

Elemental analysis, for C$_8$H$_8$N$_3$O$_4$SCl: Calcd. C, 34.60; H, 2.90; N, 15.13: Found C, 34.97; H, 3.03; N, 14.74.

NMR spectrum (60 MHz, in d$_6$-DMSO): 3.95 ppm(3H, singlet, =NOCH$_3$), 4.40 ppm(2H, singlet, ClCH$_2$CO), 7.57 ppm (1H, singlet, thiazole 5-H).

What we claim is:

1. A compound of the formula:

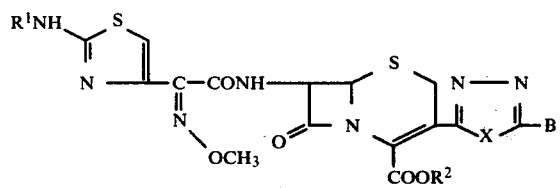

wherein R$^1$NH is an amino group R$^2$ is hydrogen or diphenylmethyl; X is sulfur; and B is an unsubstituted or substituted, hydroxyl, amino, thiol, carbamoyl, C$_{1-4}$ alkyl, benzyl, phenyl or naphthyl, the substituent being one or two members selected from the group consisting of C$_{1-4}$ alkyl, C$_{2-5}$ acyl, benzyl, phenyl and naphthyl and pharmacologically and pharmaceutically acceptable salts thereof.

2. A compound as claimed in claim 1, wherein B is an amino group or amino substituted with C$_{1-4}$ alkyl, C$_{2-5}$ acyl, benzyl or phenyl.

3. A compound as claimed in claim 1, wherein B is mono- or di-C$_{1-4}$ alkylamino or C$_{2-5}$ acylamino group.

4. A compound as claimed in claim 1, wherein the pharmacologically and pharmaceutically acceptable salt is a nontoxic alkali metal salt, a basic amino acid salt, a polyhydroxyalkylamino salt selected from the group consisting of N-methylglucamine; diethanolamine; triethanolamine; and trishydroxymethylamino, an inorganic acid salt or an organic acid salt selected from the group consisting of maleic acid and oxalic acid.

5. A compound as claimed in claim 1, which is 7-[2-(2-aminothiazol-4-yl)-2-(syn)-methoxyiminoacetamido]-3-(5-acetamido-1,3,4-thiadiazol-2-yl)-3-cephem-4-carboxylic acid.

6. An anti-bacterial composition consisting essentially of a pharmaceutically effective amount of a compound as claimed in claim 1, together with a pharmaceutically acceptable carrier or carriers therefor, said composition being administrable in a unit dose.

7. A method for the treatment of diseases caused by bacteria, which comprises internally administering to a mammal a pharmaceutically effective amount of a compound as claimed in claim 1.

* * * * *